US012617804B2

(12) United States Patent
Zhao et al.

(10) Patent No.: US 12,617,804 B2
(45) Date of Patent: May 5, 2026

(54) CONJUGATION-FUSED BIPOLAR REDOX-ACTIVE MOLECULE, PREPARATION METHOD, AND APPLICATION THEREOF

(71) Applicant: Hangzhou Normal University, Hangzhou (CN)

(72) Inventors: Yu Zhao, Hangzhou (CN); Gaole Dai, Hangzhou (CN); Yue Liu, Hangzhou (CN); Jing Ye, Hangzhou (CN); Huamei Li, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 910 days.

(21) Appl. No.: 17/893,081

(22) Filed: Aug. 22, 2022

(65) Prior Publication Data

US 2023/0136155 A1 May 4, 2023

(30) Foreign Application Priority Data

Nov. 1, 2021 (CN) ......................... 202111282577.2

(51) Int. Cl.
*C07D 513/06* (2006.01)
*H01M 8/18* (2006.01)

(52) U.S. Cl.
CPC .......... *C07D 513/06* (2013.01); *H01M 8/188* (2013.01); *H01M 2300/0025* (2013.01)

(58) Field of Classification Search
None
See application file for complete search history.

(56) References Cited

FOREIGN PATENT DOCUMENTS

| | | | |
|---|---|---|---|
| CN | 101416344 | A | 4/2009 |
| CN | 108264516 | A | 7/2018 |

OTHER PUBLICATIONS

Cayman Chem, Quinolactacin A, captured Dec. 12, 2025 (Year: 2025).*
Gilman et al. "The Metalation of Phenothiazine" Journal of the American Chemical Society (1944), 66, 625-7 (Year: 1944).*
Geysens et al. "Highly Soluble 1,4-Diaminoanthraquinone Derivative for Nonaqueous Symmetric Redox Flow Batteries" ACS Sustainable Chem. Eng. 2020, 8, 3832-3843 (Year: 2020).*

* cited by examiner

*Primary Examiner* — Adam C Milligan
*Assistant Examiner* — Jed A Kucharczk

(57) ABSTRACT

The present disclosure discloses a conjugation-fused bipolar redox-active molecule and its preparation method and application. The bipolar redox-active molecule includes a p-type redox active center and an n-type redox active center. The p-type redox active center and the n-type redox active center are fused in a molecular unit by conjugation.

2 Claims, 12 Drawing Sheets

CONJUGATION-FUSED BIPOLAR REDOX-ACTIVE MOLECULE, PREPARATION METHOD, AND APPLICATION THEREOF

CROSS REFERENCE TO RELATED APPLICATIONS

This application claims foreign priority of Chinese Patent Application No. 202111282577.2, filed on Nov. 1, 2021 in the China National Intellectual Property Administration, the disclosures of all of which are hereby incorporated by reference.

TECHNICAL FIELD

The present disclosure relates to the field of organic electrode material technologies, and in particular to a conjugation-fused bipolar redox-active molecule, a preparation method, and an application thereof.

BACKGROUND

Redox flow batteries (RFBs) are considered as one of the most promising electrochemical energy storage technologies for grid-scale energy storage, with significant advantages such as safety, long life, flexible configuration, and their power and energy density can be independently configured. RFBs currently under development have shown significant improvements in various aspects, but still have limitations such as low output voltage, cross-contamination between cathode and anode electrolytes, and low solubility of active materials.

Unlike conventional redox-active organic molecules (ROMs), organic bipolar redox-active molecules (BRMs) can either lose electrons first and undergo an oxidation reaction or gain electrons first and undergo a reduction reaction, and the two redox reactions can proceed independently and are reversible. Therefore, the same redox-active molecules and electrolyte can be utilized in each half-cell component of formed symmetric redox flow batteries (SRFBs). This configuration can effectively reduce the chemical concentration gradient on both sides of the membrane of the flow batteries, which can mitigate the cross-contamination. Even if some of the active materials on both sides permeate during charging and discharging, the SRFBs can return to their initial state by self-discharge without irreversible effects. This is theoretically beneficial to improve the utilization efficiency of the BRMs and extend the lifetime of the RFBs, and these remarkable properties make the SRFBs promising for storage technology.

Currently, the research on BRMs is mainly focused on screening and exploring new molecules with multiple redox reactions, as well as modifying existing BRMs to improve their solubility and stability. The modification strategies include forming bipolar eutectic mixtures, combining different types of redox-active molecules through covalent bonding or improving solubility or stability by introducing functionalized functional groups. These strategies extend the application of BRMs in RFBs and improve the solubility or structural stability of the materials. However, the current research on BRMs does not go beyond the traditional pairing of cathode and anode materials for organic flow batteries, and lacks the regulation of chemical/electrochemical properties of BRMs, such as the regulation of redox potential or redox reversibility. In particular, it does not change the lower output voltage of SRFBs, i.e., the voltage gap between the two redox reactions of BRMs is small, which cannot better exploit the advantages of all-organic-phase flow batteries.

SUMMARY OF THE DISCLOSURE

In order to solve the above technical problems, the present disclosure provides a conjugation-fused bipolar redox-active molecule and its preparation method and application. The present disclosure conjugately fuses two redox-active centers into one molecular unit, which may realize the regulation of redox potential of bipolar redox-active molecules and increase the output voltage of redox flow battery.

Specific technical solution proposed are as followed.

In a first aspect, the present disclosure provides a conjugation-fused bipolar redox-active molecule, comprising a p-type redox active center and an n-type redox active center; wherein the p-type redox active center and the n-type redox active center are fused in a molecular unit by conjugation.

The bipolar redox-active molecules can be used in symmetric redox flow batteries (SRFBs) as active materials in both cathode and anode electrolytes of the batteries, which can effectively reduce the chemical concentration gradient on both sides of the membrane of the flow batteries, mitigating the cross-contamination. Even if some of the active materials on both sides permeate during charging and discharging, the SRFBs can return to their initial state by self-discharge without irreversible effects. This is theoretically beneficial to improve the utilization efficiency of the BRMs and extend the lifetime of the RFBs.

Moreover, the present disclosure fuses different types (p-type and n-type) of redox-active centers into one molecular unit by conjugation, and achieves the regulation of redox potential of BRMs by the intra-molecular charge transfer effect. The specific mechanism is shown in FIG. 1: after conjugate fusion of two redox-active centers, the electron cloud around the p-type active center (e.g., quaternary nitrogen) is attracted by the n-type active center (e.g., carbonyl ketone), thereby weakening its electron effect; while the electron density around the n-type active center is enhanced by the electron-donating effect from the p-type. Therefore, during the oxidation of the p-type active center, its redox potential increases due to the negative charge compensation being hindered in the presence of the electron-withdrawing n-type active center; similarly, the positive charge compensation of the n-type active center is hindered by the electron donating effect of the p-type active center, leading to a decrease in the redox potential of the n-type active center in this structure. Therefore, when the bipolar redox-active molecules (BRMs) of the present disclosure are used as both cathode and anode electrolyte components of SRFB, the potential separation of the two half-reactions increases, i.e., the output voltage of the whole battery increases. By exploiting this synergistic effect of expanding the potential difference between the two redox-active centers, this kind of BRMs facilitates the achievement of high output voltages when applied to SRFBs.

In addition, the conjugate fusion of different types of redox-active centers may extend the conjugate structure of the molecule and facilitate the electron leaving domain within the molecule, thereby enhancing the stability of the molecule and its redox reaction intermediates.

In some embodiments, the p-type redox active center is a quaternary nitrogen and the n-type redox active center is a carbonyl ketone.

In some embodiments, the molecule has a structural formula as followed.

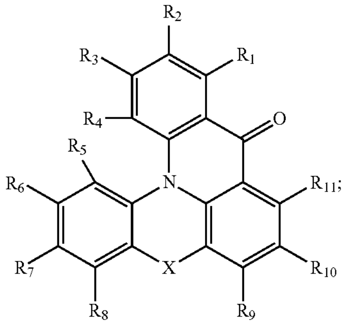

wherein the R1 to R12 are identical or different from each other and are each independently selected from —H and polar functional groups; the X is a third main group element or a fifth main group element.

In the above structure, the n-type and p-type active centers are conjugated to each other, which may regulate the electron distribution of redox-active centers through electron leaving domains and charge-inducing effects while extending the molecular conjugation system to enhance the molecular stability, thereby realizing the regulation of intramolecular charges.

In addition, the presence of element X may lock the two benzene rings connected by the quaternary nitrogen active center, which may extend the whole molecular planarity and improve the overall conjugation degree, thereby improving the overall molecular stability.

In some embodiments, the structural formula is as followed.

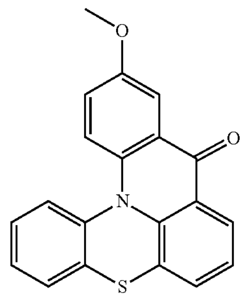 [SMILES: COc1ccc2c(c1)c(=O)c1cccc3c1n2-c1ccccc1S3]

The bipolar redox-active molecule (QPT-OMe) with the above structure exhibits an electrochemical window close to 3 V, which is better than most "bipolar" battery active materials. In addition, the QPT-OMe is able to increase its solubility in electrolyte solvents by introducing polar methoxy functional groups, thereby obtaining a "bipolar" battery active material with high solubility, high stability and high voltage.

In some embodiments, the structural formula is as followed.

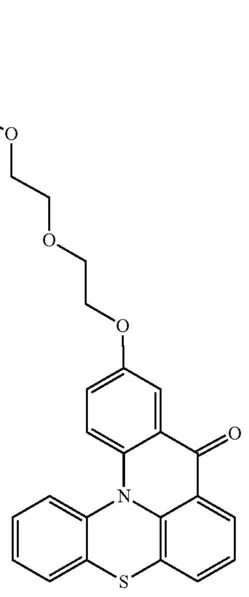

The bipolar redox-active molecule with the above structure (QPT-TEG) is a mucoadhesive fluid that is miscible with most polar organic solvents. QPT-TEG is able to increase the overall solubility of the molecule by introducing long ether chains without changing the redox potential of the designed redox subject molecule. It is proved by tests that QPT-TEG can be miscible with acetonitrile, dimethyl sulfoxide, dichloromethane and other solvents in any ratio.

In a second aspect, the present disclosure provides a method for preparing a conjugation-fused bipolar redox-active molecule (QPT-OMe), the method comprises the following steps.

mixing 10H-phenothiazine (1), methyl 2-bromo-5-methoxybenzoate (2), cesium carbonate, platinum(II) acetate ($Pd(OAc)_2$), 2-dicyclohexylphosphino-2',4',6'-triisopropylbiphenyl (XPhos), and o-xylene and removing oxygen to obtain a first mixture, and heating the first mixture at 125~135° C. for 20~28 h to obtain a first product; separating the first product to obtain 5-m ethoxy-2-(10H-phenothiazin-10-yl)benzoate (3).

mixing the methyl 5-methoxy-2-(10H-phenothiazin-10-yl)benzoate (3), NaOH, H2O, and 1, 4-dioxane to obtain a second mixture, and heating the second mixture under inert atmosphere at 90~110° C. for 10~14 h to obtain a second product; separating the second product to obtain 5-methoxy-2-(10H-phenothiazin-10-yl)benzoic acid (4).

mixing the 5-methoxy-2-(10H-phenothiazin-10-yl)benzoic acid (4) and polyphosphoric acid to obtain a third mixture, and heating the third mixture under inert atmosphere at 140~150° C. for 10~14 h to obtain a third product; separating the third product to obtain the conjugation-fused bipolar redox-active molecule (QPT-OMe).

The synthetic route for the above preparation process is as follows.

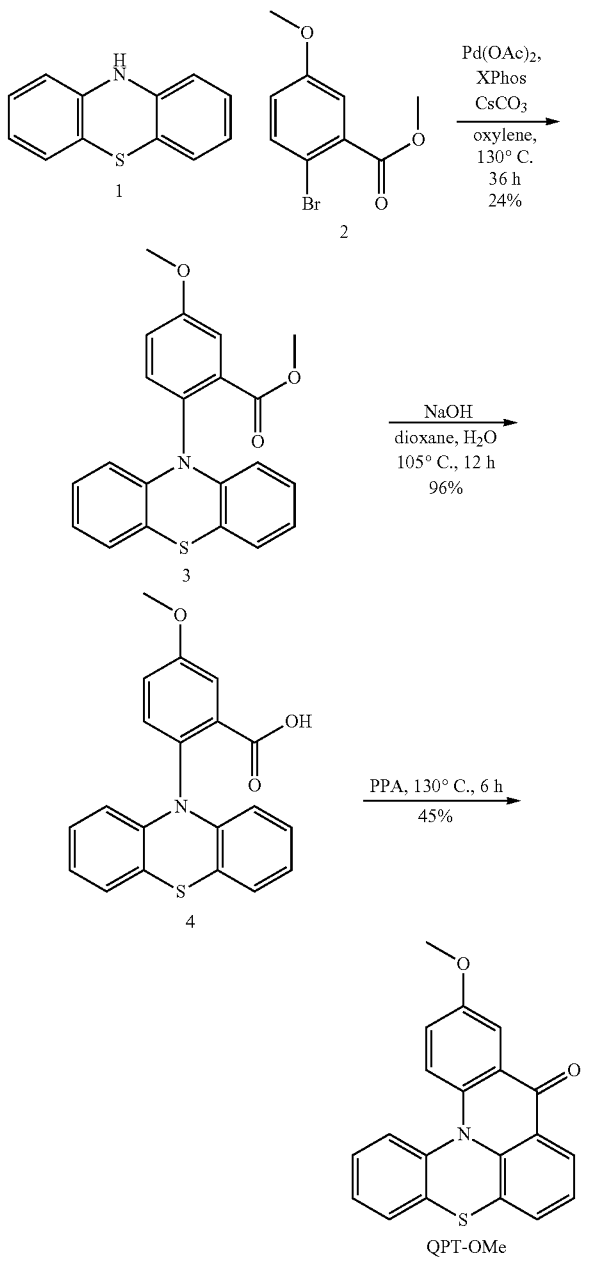

1 2 3 4

QPT-OMe

The synthetic route for the above preparation process is as follows.

In a third aspect, the present disclosure provides a method for preparing a conjugation-fused bipolar redox-active molecule (QPT-TEG), the method comprises the following steps.

mixing 10H-phenothiazine (1), methyl 2-bromo-5-fluorobenzoate (5), cesium carbonate, Pd(OAc)$_2$, 2-dicyclohexylphosphino-2',4',6'-triisopropylbiphenyl, and o-xylene and removing oxygen to obtain a fourth mixture, and heating the fourth mixture at 125~135° C. for 20~28 h to obtain a fourth product; separating the fourth product to obtain methyl 5-fluoro-2-(10H-phenothiazin-10-yl)benzoate (6).

mixing the methyl 5-fluoro-2-(10H-phenothiazin-10-yl) benzoate (6), NaOH, H2O, and 1, 4-dioxane to obtain a fifth mixture and heating the fifth mixture under inert atmosphere at 90~110° C. for 10~14 h to obtain a fifth product; separating the fifth product to obtain 5-fluoro-2-(10H-phenothiazin-10-yl)benzoic acid (7).

mixing the 5-fluoro-2-(10H-phenothiazin-10-yl)benzoic acid (7) and polyphosphoric acid to obtain a sixth mixture, and heating the sixth mixture under inert atmosphere at 140~150° C. for 10~14 h to obtain a sixth product; separating the sixth product to obtain 11-fluoro-9H-quinolo[3,2,1-kl]phenothiazin-9-one (8).

mixing the 11-fluoro-9H-quinolo[3,2,1-kl]phenothiazine-9-one (8), triethylene glycol monomethyl ether, NaH, and N,N-dimethylformamide to obtain a seventh mixture, and heating the seventh mixture under inert atmosphere and 75~85° C. for 10~14 h to obtain a seventh product; separating the seventh product to obtain the conjugation-fused bipolar redox-active molecule (QPT-TEG).

The synthetic route for the above preparation process is as follows.

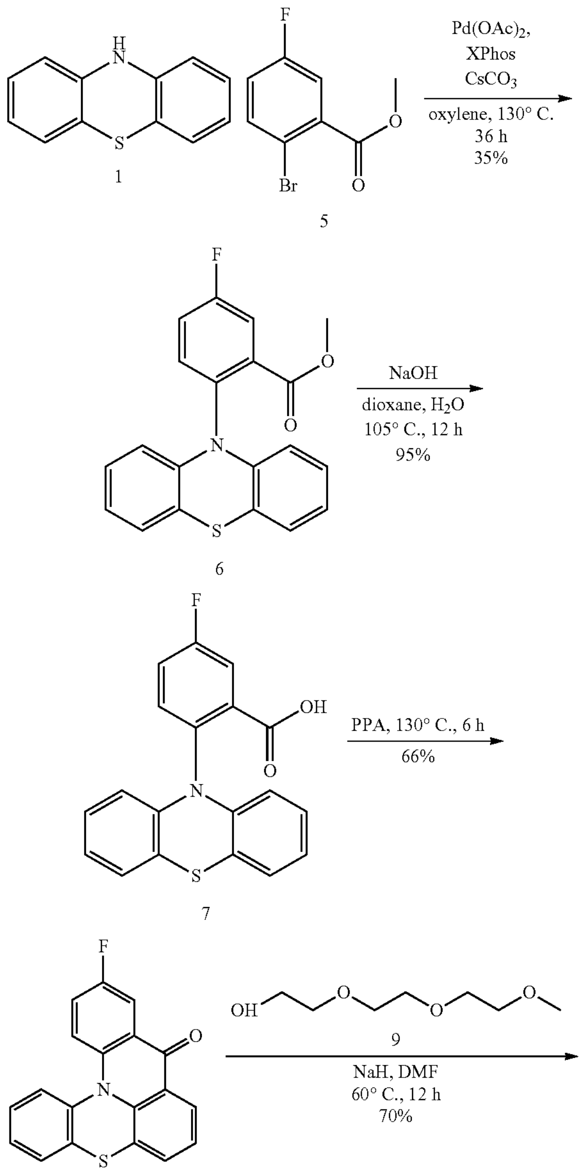

1 5 6 7

-continued

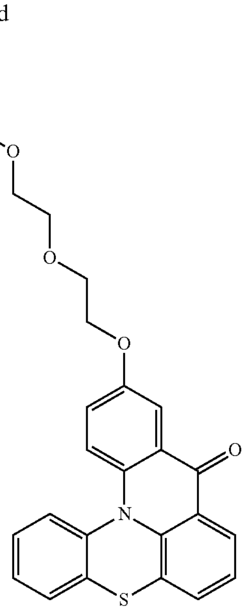

QPT-TEG

In a fourth aspect, the present disclosure provides a symmetric redox flow battery, comprising a cathode electrolyte and an anode electrolyte; wherein the cathode electrolyte and the anode electrolyte both contain the conjugation-fused bipolar redox-active molecule.

In some embodiments, the cathode electrolyte and the anode electrolyte both further contain an electrolyte salt and an organic solvent.

In some embodiments, the organic solvent includes one or more of ethylene glycol dimethyl ether, 1,3 dioxolane, vinyl carbonate, propylene carbonate, dimethyl carbonate, diethyl carbonate and dimethyl sulfoxide, further preferably acetonitrile.

In some embodiments, the battery is a static flow battery or a dynamic flow battery.

Static and dynamic flow batteries are the two common types of symmetric redox flow batteries.

The static liquid flow batteries include cathode and anode terminal plates, cathode and anode collectors, porous membranes, cathode, anode, cathode and anode reservoirs, and sealant. When the battery in use, the same volume of electrolyte is injected into the cathode and anode reservoirs and the battery is pressed. When charging and discharging for the first time, the cathode and anode of the battery are not distinguished and can be switched; after the first charging and discharging, the cathode and anode are distinguished. During use, the charging and discharging polarity is changed, and the battery can return to normal use after the complete charging and discharging process.

The dynamic liquid flow battery includes cathode and anode terminal plates, cathode and anode reservoirs, cathode and anode collectors, circulation pump, and circulation pipeline. When the battery in use, the same volume of electrolyte is injected into the cathode and anode reservoirs, and then the circulation pump is started so that the electrolyte in the reservoirs flows through the battery frame via the circulation pipeline and is always circulated. The bipolar active materials in the electrolyte undergo redox reactions in the area of flowing through the battery collectors, and the oxidized or reduced materials flow into the reservoir until the entire liquid in the reservoir is fully oxidized or reduced. When the battery is first charged and discharged, the cathode and anode are not distinguished and can be switched; after the first charge and discharge, the cathode and anode are distinguished. During use, the charging and discharging polarity is changed, and the battery can return to normal use after the complete charging and discharging process.

Both static and dynamic flow batteries made with the bipolar redox-active molecules of the present disclosure are free of cross-contamination and have high cycle efficiency, high output voltage, long cycle life and good capacity stability.

Compared with the prior art, the present disclosure has the following advantages.

(1) the bipolar redox-active molecules of the present disclosure conjugately fuse p-type and n-type redox active centers into one molecular unit, which may achieve the regulation of redox potential and increase the voltage gap between its two redox reactions, thereby increasing the output voltage of the redox flow battery.

(2) The two bipolar redox-active molecules QPT-OMe and QPT-TEG of the present disclosure have high solubility in the electrolyte solvent and good stability, and can effectively increase the output voltage of the flow battery.

DETAILED DESCRIPTION

Figure 1:
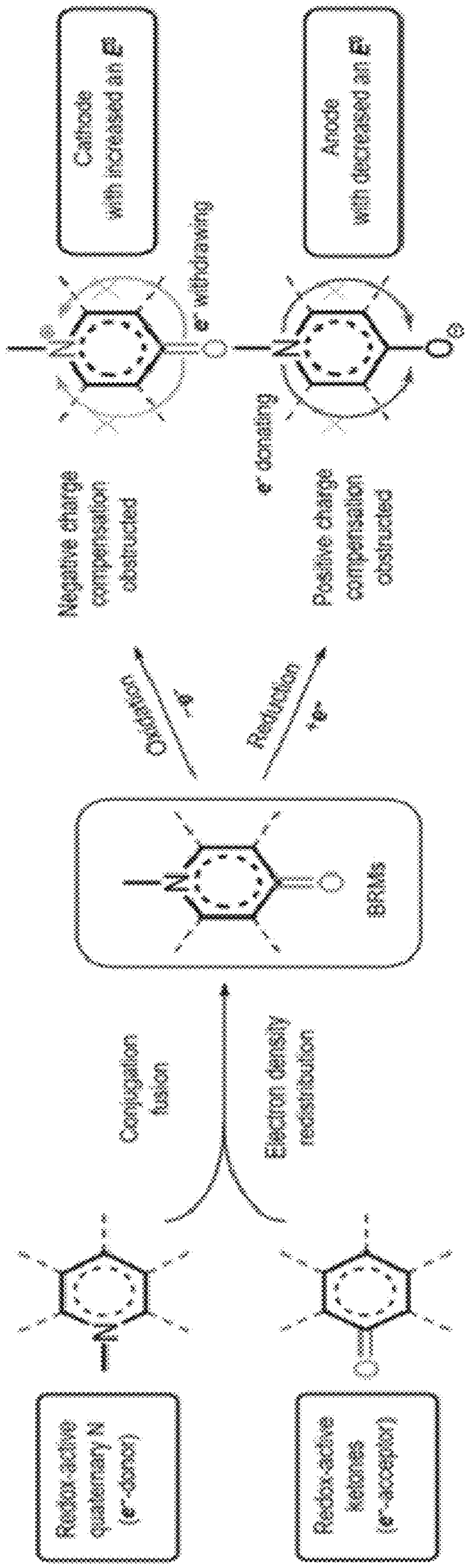
FIG. 1 is a schematic diagram of charge transfer of a conjugation-fused bipolar redox-active molecule.

The present disclosure is further described below in conjunction with embodiments.

Embodiment 1

A conjugation-fused bipolar redox-active molecule (QPT-OMe) with the following structural formula.

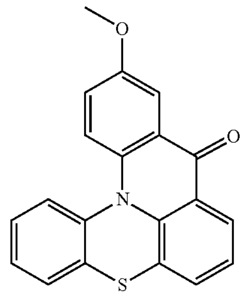 [SMILES: COc1ccc2c(c1)c(=O)c1cccc3c1n2-c1ccccc1S3]

QPT-OMe may be prepared by the following steps.

(1) Synthesis of methyl 5-methoxy-2-(10H-phenothiazin-10-yl)benzoate

A mixture of 10H-phenothiazine (0.796 g, 4.0 mmol), methyl 2-bromo-5-methoxybenzoate (1.029 g, 4.2 mmol), cesium carbonate (3.910 g, 12.0 mmol), catalyst $Pd(OAc)_2$ (90 mg), and ligand XPhos (381 mg) is added to o-xylene (40 mL), degassed by freezing-pumping-thawing, charged with nitrogen, and heated to react at 130° C. for 24 h. After the reaction is completed, the resultant is cooled to room temperature, extracted with dichloromethane (DCM), and the mixed organic phase is collected and concentrated to obtain a crude product, which is later purified by silica gel column chromatography to obtain a yellow solid, methyl 5-methoxy-2-(10H-phenothiazin-10-yl)benzoate, in a yield of 24%.

(2) Synthesis of 5-methoxy-2-(10H-phenothiazin-10-yl)benzoic acid

Methyl 5-methoxy-2-(10H-phenothiazin-10-yl)benzoate (0.544 g, 1.5 mmol), NaOH (0.480 g, 12 mmol), $H_2O$ (10 mL), and 1,4-dioxane (20 mL) are mixed and heated under nitrogen atmosphere at 100° C. for 12 h. After the reaction is completed, the resultant is cooled to room temperature and aqueous hydrogen chloride solution (1 M) is added dropwise until a white solid precipitate is formed and the pH is less than 1. Filtration is performed and a resulting solid is washed completely with water to obtain a product of 96% purity, namely 5-methoxy-2-(10H-phenothiazin-10-yl)benzoic acid.

(3) Synthesis of QPT-OMe 5-methoxy-2-(10H-phenothiazin-10-yl)benzoic acid and polyphosphoric acid (PAA) (50 mL) are mixed and heated under nitrogen atmosphere at 140° C. for 12 h. After the reaction is completed, the resultant is cooled to room temperature and is added with ice water (200 mL) dropwise and then extracted with DCM. The organic phase is collected, dried with anhydrous magnesium sulfate, and concentrated. A crude product is purified by silica gel column chromatography to obtain a yellow solid, QPT-OMe, in a yield of 45%.

Embodiment 2

A conjugation-fused bipolar redox-active molecule (QPT-OMe) with the following structural formula.

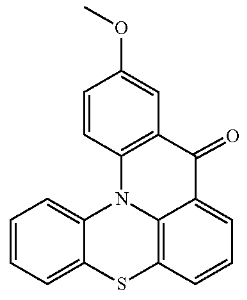 [SMILES: COc1ccc2c(c1)c(=O)c1cccc3c1n2-c1ccccc1S3]

QPT-OMe may be prepared by the following steps.

(1) Synthesis of methyl 5-methoxy-2-(10H-phenothiazin-10-yl)benzoate

A mixture of 10H-phenothiazine (0.796 g, 4.0 mmol), methyl 2-bromo-5-methoxybenzoate (0.931 g, 3.8 mmol), cesium carbonate (3.258 g, 10.0 mmol), catalyst $Pd(OAc)_2$ (85 mg), and ligand XPhos (370 mg) is added to o-xylene (35 mL), degassed by freezing-pumping-thawing, charged with nitrogen, and heated to react at 125° C. for 28 h. After the reaction is completed, the resultant is cooled to room temperature, extracted with dichloromethane (DCM), and the mixed organic phase is collected and concentrated to obtain a crude product, which is later purified by silica gel column chromatography to obtain a yellow solid, methyl 5-methoxy-2-(10H-phenothiazin-10-yl)benzoate.

(2) Synthesis of 5-methoxy-2-(10H-phenothiazin-10-yl)benzoic acid

Methyl 5-methoxy-2-(10H-phenothiazin-10-yl)benzoate (0.544 g, 1.5 mmol), NaOH (0.400 g, 10 mmol), $H_2O$ (8 mL), and 1,4-dioxane (16 mL) are mixed and heated under nitrogen atmosphere at 90° C. for 14 h. After the reaction is completed, the resultant is cooled to room temperature and aqueous hydrogen chloride solution (0.8 M) is added dropwise until a white solid precipitate is formed and the pH is less than 1. Filtration is performed and a resulting solid is washed completely with water to obtain a product, namely 5-methoxy-2-(10H-phenothiazin-10-yl)benzoic acid.

(3) Synthesis of QPT-OMe 5-methoxy-2-(10H-phenothiazin-10-yl)benzoic acid and polyphosphoric acid (PAA) (47 mL) are mixed and heated under nitrogen atmosphere at 145° C. for 14 h. After the reaction is completed, the resultant is cooled to room temperature and is added with ice water (200 mL) dropwise and then extracted with DCM. The organic phase is collected, dried with anhydrous magnesium sulfate, and concentrated. A crude product is purified by silica gel column chromatography to obtain a yellow solid, QPT-OMe.

Embodiment 3

A conjugation-fused bipolar redox-active molecule (QPT-OMe) with the following structural formula.

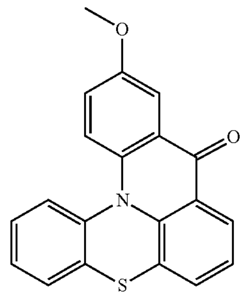 [SMILES: COc1ccc2c(c1)c(=O)c1cccc3c1n2-c1ccccc1S3]

QPT-OMe may be prepared by the following steps.

(1) Synthesis of methyl 5-methoxy-2-(10H-phenothiazin-10-yl)benzoate

A mixture of 10H-phenothiazine (0.796 g, 4.0 mmol), methyl 2-bromo-5-methoxybenzoate (0.980 g, 4.0 mmol), cesium carbonate (4.888 g, 15.0 mmol), catalyst $Pd(OAc)_2$ (93 mg), and ligand XPhos (385 mg) is added to o-xylene (45 mL), degassed by freezing-pumping-thawing, charged with nitrogen, and heated to react at 130° C. for 20 h. After the reaction is completed, the resultant is cooled to room temperature, extracted with dichloromethane (DCM), and the mixed organic phase is collected and concentrated to obtain a crude product, which is later purified by silica gel column chromatography to obtain a yellow solid, methyl 5-methoxy-2-(10H-phenothiazin-10-yl)benzoate, in a yield of 24%.

(2) Synthesis of 5-methoxy-2-(10H-phenothiazin-10-yl)benzoic acid

Methyl 5-methoxy-2-(10H-phenothiazin-10-yl)benzoate (0.544 g, 1.5 mmol), NaOH (0.600 g, 15 mmol), $H_2O$ (13 mL), and 1,4-dioxane (25 mL) are mixed and heated under nitrogen atmosphere at 110° C. for 10 h. After the reaction is completed, the resultant is cooled to room temperature and aqueous hydrogen chloride solution (1.2 M) is added dropwise until a white solid precipitate is formed and the pH is less than 1. Filtration is performed and a resulting solid is washed completely with water to obtain a product of 96% purity, namely 5-methoxy-2-(10H-phenothiazin-10-yl)benzoic acid.

(3) Synthesis of QPT-OMe 5-methoxy-2-(10H-phenothiazin-10-yl)benzoic acid and polyphosphoric acid (PAA) (55 mL) are mixed and heated under nitrogen atmosphere at 150° C. for 10 h. After the reaction is completed, the resultant is cooled to room temperature and is added with ice water (200 mL) dropwise and then extracted with DCM. The organic phase is collected, dried with anhydrous magnesium sulfate, and concentrated. A crude product is purified by silica gel column chromatography to obtain a yellow solid, QPT-OMe, in a yield of 45%.

Embodiment 4

A conjugation-fused bipolar redox-active molecule (QPT-TEG) with the following structural formula.

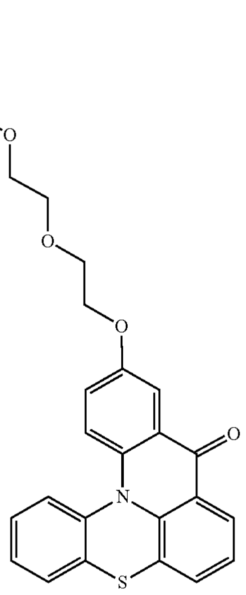

QPT-TEG may be prepared by the following steps.

(1) Synthesis of methyl 5-fluoro-2-(10H-phenothiazin-10-yl)benzoate

A mixture of 10H-phenothiazine (0.796 g, 4.0 mmol), methyl 2-bromo-5-fluorobenzoate (0.979 g, 4.2 mmol), cesium carbonate (3.910 g, 12.0 mmol), catalyst $Pd(OAc)_2$ (90 mg) and ligand XPhos (381 mg) is added to o-xylene (40 mL), degassed by freezing-pumping-thawing, charged with nitrogen, and heated to react at 130° C. for 24 h. After the reaction is completed, the resultant is cooled to room temperature, extracted with dichloromethane (DCM), and the mixed organic phase is collected and concentrated to obtain a crude product, which is later purified by silica gel column chromatography to obtain a yellow solid, methyl 5-fluoro-2-(10H-phenothiazin-10-yl)benzoate, in a yield of 35%.

(2) Synthesis of 5-methoxy-2-(10H-phenothiazin-10-yl)benzoic acid

Methyl 5-methoxy-2-(10H-phenothiazin-10-yl)benzoate (0.702 g, 2.0 mmol), NaOH (0.480 g, 12 mmol), $H_2O$ (10 mL), and 1,4-dioxane (20 mL) are mixed and heated under nitrogen atmosphere at 100° C. for 12 h. After the reaction is completed, the resultant is cooled to room temperature and aqueous hydrogen chloride solution (1 M) is added dropwise until a white solid precipitate is formed and the pH is less than 1. Filtration is performed and a resulting solid is washed completely with water to obtain a product of 96% purity, namely 5-methoxy-2-(10H-phenothiazin-10-yl)benzoic acid.

(3) Synthesis of 11-fluoro-9H-quinolo[3,2,1-kl]phenothiazin-9-one

5-Fluoro-2-(10H-phenothiazin-10-yl)benzoic acid (0.505 g, 1.5 mmol) and polyphosphoric acid (50 mL) are mixed and heated under nitrogen atmosphere at 140° C. for 12 h. After the reaction is completed, the resultant is cooled to room temperature and is added with ice water (200 mL) dropwise and then extracted with DCM. The organic phase is collected, dried with anhydrous magnesium sulfate, and concentrated. A crude product is purified by silica gel column chromatography to obtain a yellow solid, 11-fluoro-9H-quinolo[3,2,1-kl]phenothiazine-9-one, in a yield of 66%.

(4) Synthesis of QPT-TEG 11-fluoro-9H-quinolinolo[3,2,1-kl]phenothiazin-9-one (0.319 g, 1.0 mmol), triglyceride monomethyl ether (0.164 g, 1.0 mmol), NaH (0.200 g, 5.0 mmol, dispersed in liquid paraffin at 60 wt % by mass), and N,N-dimethylformamide (DMF) are mixed and heated under nitrogen atmosphere at 80° C. for 12 h. After the reaction is completed, the resultant is cooled to room temperature and is extracted with DCM. The organic phase is collected, dried with anhydrous magnesium sulfate, and concentrated. A crude product is purified by silica gel column chromatography to obtain an orange colloidal liquid, QPT-TEG, in a yield of 70%.

Embodiment 5

A conjugation-fused bipolar redox-active molecule (QPT-TEG) with the following structural formula.

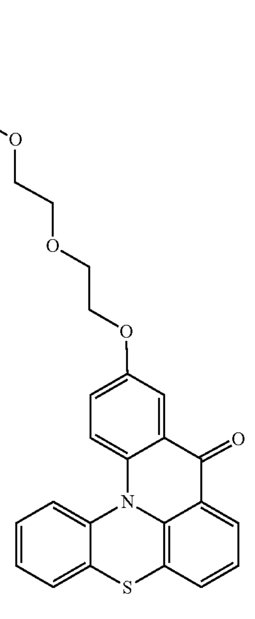

QPT-TEG may be prepared by the following steps.

(1) Synthesis of methyl 5-fluoro-2-(10H-phenothiazin-10-yl)benzoate

A mixture of 10H-phenothiazine (0.796 g, 4.0 mmol), methyl 2-bromo-5-fluorobenzoate (0.886 g, 3.8 mmol), cesium carbonate (3.258 g, 10.0 mmol), catalyst $Pd(OAc)_2$ (85 mg) and ligand XPhos (370 mg) is added to o-xylene (35 mL), degassed by freezing-pumping-thawing, charged with nitrogen, and heated to react at 125° C. for 28 h. After the reaction is completed, the resultant is cooled to room temperature, extracted with dichloromethane (DCM), and the mixed organic phase is collected and concentrated to obtain a crude product, which is later purified by silica gel column chromatography to obtain a yellow solid, methyl 5-fluoro-2-(10H-phenothiazin-10-yl)benzoate.

(2) Synthesis of 5-methoxy-2-(10H-phenothiazin-10-yl)benzoic acid

Methyl 5-methoxy-2-(10H-phenothiazin-10-yl)benzoate (0.702 g, 2.0 mmol), NaOH (0.400 g, 10 mmol), $H_2O$ (8 mL), and 1,4-dioxane (16 mL) are mixed and heated under nitrogen atmosphere at 90° C. for 14 h. After the reaction is completed, the resultant is cooled to room temperature and aqueous hydrogen chloride solution (1 M) is added dropwise until a white solid precipitate is formed and the pH is less than 1. Filtration is performed and a resulting solid is washed completely with water to obtain a product of 96% purity, namely 5-methoxy-2-(10H-phenothiazin-10-yl)benzoic acid.

(3) Synthesis of 11-fluoro-9H-quinolo[3,2,1-kl]phenothiazin-9-one

5-Fluoro-2-(10H-phenothiazin-10-yl)benzoic acid (0.505 g, 1.5 mmol) and polyphosphoric acid (47 mL) are mixed and heated under nitrogen atmosphere at 145° C. for 14 h. After the reaction is completed, the resultant is cooled to room temperature and is added with ice water (200 mL) dropwise and then extracted with DCM. The organic phase is collected, dried with anhydrous magnesium sulfate, and concentrated. A crude product is purified by silica gel column chromatography to obtain a yellow solid, 11-fluoro-9H-quinolo[3,2,1-kl]phenothiazine-9-one.

(4) Synthesis of QPT-TEG 11-fluoro-9H-quinolinolo[3,2,1-kl]phenothiazin-9-one (0.319 g, 1.0 mmol), triglyceride monomethyl ether (0.197 g, 1.2 mmol), NaH (0.212 g, 5.3 mmol, dispersed in liquid paraffin at 60 wt % by mass), and N,N-dimethylformamide (DMF) are mixed and heated under nitrogen atmosphere at 80° C. for 12 h. After the reaction is completed, the resultant is cooled to room temperature and is extracted with DCM. The organic phase is collected, dried with anhydrous magnesium sulfate, and concentrated. A crude product is purified by silica gel column chromatography to obtain an orange colloidal liquid, QPT-TEG.

Embodiment 6

A conjugation-fused bipolar redox-active molecule (QPT-TEG) with the following structural formula.

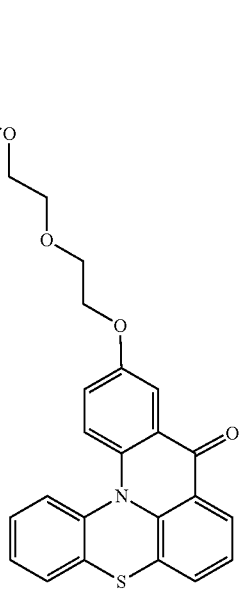

QPT-TEG may be prepared by the following steps.

(1) Synthesis of methyl 5-fluoro-2-(10H-phenothiazin-10-yl)benzoate

A mixture of 10H-phenothiazine (0.796 g, 4.0 mmol), methyl 2-bromo-5-fluorobenzoate (0.932 g, 4.0 mmol), cesium carbonate (4.888 g, 15.0 mmol), catalyst $Pd(OAc)_2$ (93 mg) and ligand XPhos (385 mg) is added to o-xylene (45 mL), degassed by freezing-pumping-thawing, charged with nitrogen, and heated to react at 130° C. for 20 h. After the reaction is completed, the resultant is cooled to room temperature, extracted with dichloromethane (DCM), and the mixed organic phase is collected and concentrated to obtain a crude product, which is later purified by silica gel column chromatography to obtain a yellow solid, methyl 5-fluoro-2-(10H-phenothiazin-10-yl)benzoate.

(2) Synthesis of 5-methoxy-2-(10H-phenothiazin-10-yl)benzoic acid

Methyl 5-methoxy-2-(10H-phenothiazin-10-yl)benzoate (0.702 g, 2.0 mmol), NaOH (0.600 g, 15 mmol), $H_2O$ (13 mL), and 1,4-dioxane (25 mL) are mixed and heated under nitrogen atmosphere at 110° C. for 10 h. After the reaction is completed, the resultant is cooled to room temperature and aqueous hydrogen chloride solution (1.2 M) is added dropwise until a white solid precipitate is formed and the pH is less than 1. Filtration is performed and a resulting solid is washed completely with water to obtain a product of 96% purity, namely 5-methoxy-2-(10H-phenothiazin-10-yl)benzoic acid.

(3) Synthesis of 11-fluoro-9H-quinolo[3,2,1-kl]phenothiazin-9-one

5-Fluoro-2-(10H-phenothiazin-10-yl)benzoic acid (0.505 g, 1.5 mmol) and polyphosphoric acid (55 mL) are mixed and heated under nitrogen atmosphere at 150° C. for 10 h. After the reaction is completed, the resultant is cooled to room temperature and is added with ice water (200 mL) dropwise and then extracted with DCM. The organic phase is collected, dried with anhydrous magnesium sulfate, and concentrated. A crude product is purified by silica gel column chromatography to obtain a yellow solid, 11-fluoro-9H-quinolo[3,2,1-kl]phenothiazine-9-one.

(4) Synthesis of QPT-TEG 11-fluoro-9H-quinolinolo[3,2,1-kl]phenothiazin-9-one (0.319 g, 1.0 mmol), triglyceride monomethyl ether (0.230 g, 1.4 mmol), NaH (0.220 g, 5.5 mmol, dispersed in liquid paraffin at 60 wt % by mass), and N,N-dimethylformamide (DMF) are mixed and heated under nitrogen atmosphere at 80° C. for 12 h. After the reaction is completed, the resultant is cooled to room temperature and is extracted with DCM. The organic phase is collected, dried with anhydrous magnesium sulfate, and concentrated. A crude product is purified by silica gel column chromatography to obtain an orange colloidal liquid, QPT-TEG, in a yield of 70%.

Test Example 1: QPT-OMe

Figure 2:
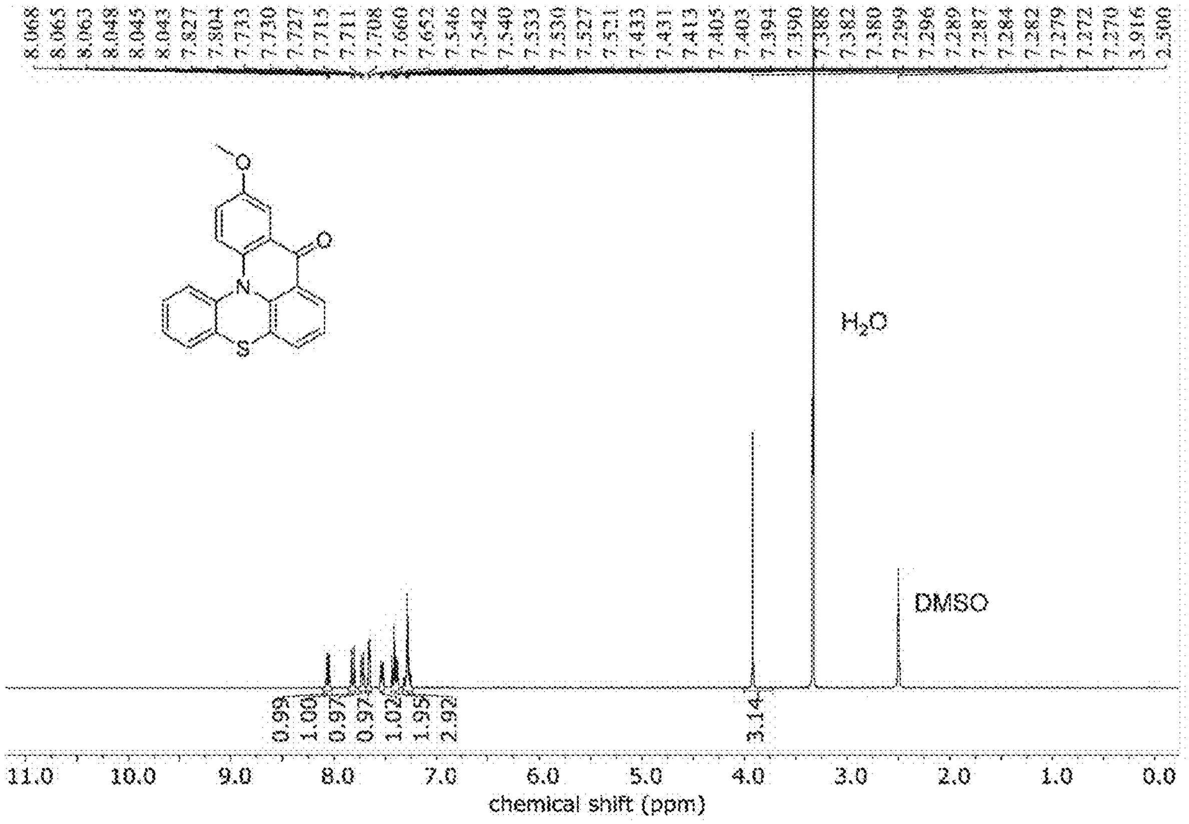
FIG. 2 is a nuclear magnetic resonance $^{1}H$ spectrum of QPT-OMe prepared in Embodiment 1.

NMR characterization of QPT-OMe obtained in Embodiment 1 is performed, and the results are shown in FIG. 2. In the NMR $^1H$ spectrum of QPT-OMe, $^1H$ NMR (400 MHz, DMSO-d6, ppm) δ=8.06 (dd, J=8.0, 1.4 Hz, 1H), 7.82 (d, J=9.2 Hz, 1H), 7.73 (dt, J=7.6, 1.3 Hz, 1H), 7.66 (d, J=3.1 Hz, 1H), 7.58-7.49 (m, 1H), 7.47-7.36 (m, 2H), 7.35-7.23 (m, 3H), 3.92 (s, 3H).

Figure 3:
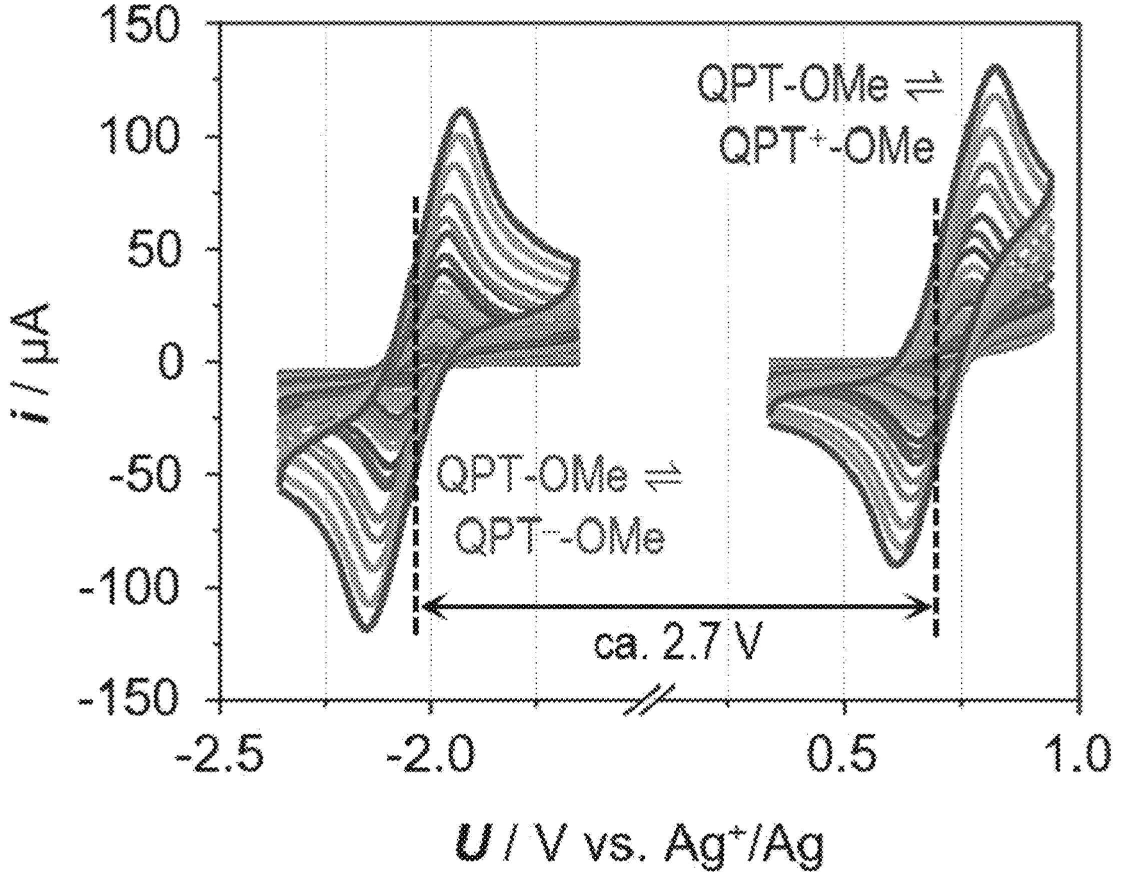
FIG. 3 is a cyclic voltammetric test curves of QPT-OMe prepared in Embodiment 1.

Redox kinetics of QPT-OMe obtained in Embodiment 1 is tested by cyclic voltammetry (CV). Tetrabutylammonium bis(trifluoromethylsulfonyl)imide (TBA-TF SI) is used as a supporting electrolyte and acetonitrile as a solvent. The results are shown in FIG. 3, where two pairs of symmetrical cathodic and anodic peaks can be clearly observed. The half-wave potentials of −2.04 and 0.72 V (with respect to $Ag^+/Ag$) correspond to the reduction and oxidation reactions of QPT-OMe, respectively. The open-circuit voltage is about 2.76 V when using QPT-OMe as the active material in the RFB, which is one of the highest value for bipolar molecules so far.

Furthermore, the QPT-OMe/QPT-OMe and QPT-P-OMe/QPT-OMe redox pairs show high rate constants of $1.4\times10^{-2}$ and 1.6x10-2 cm $s^{-1}$, respectively, by calculation. This is probably due to the relatively low recombination energy required for single electron transfer to occur from a large off-domain π-conjugated system. The high rate constants also imply negligible voltage loss when electrochemical reactions occur at the electrode surface.

Test Example 2: QPT-TEG

Figure 4:
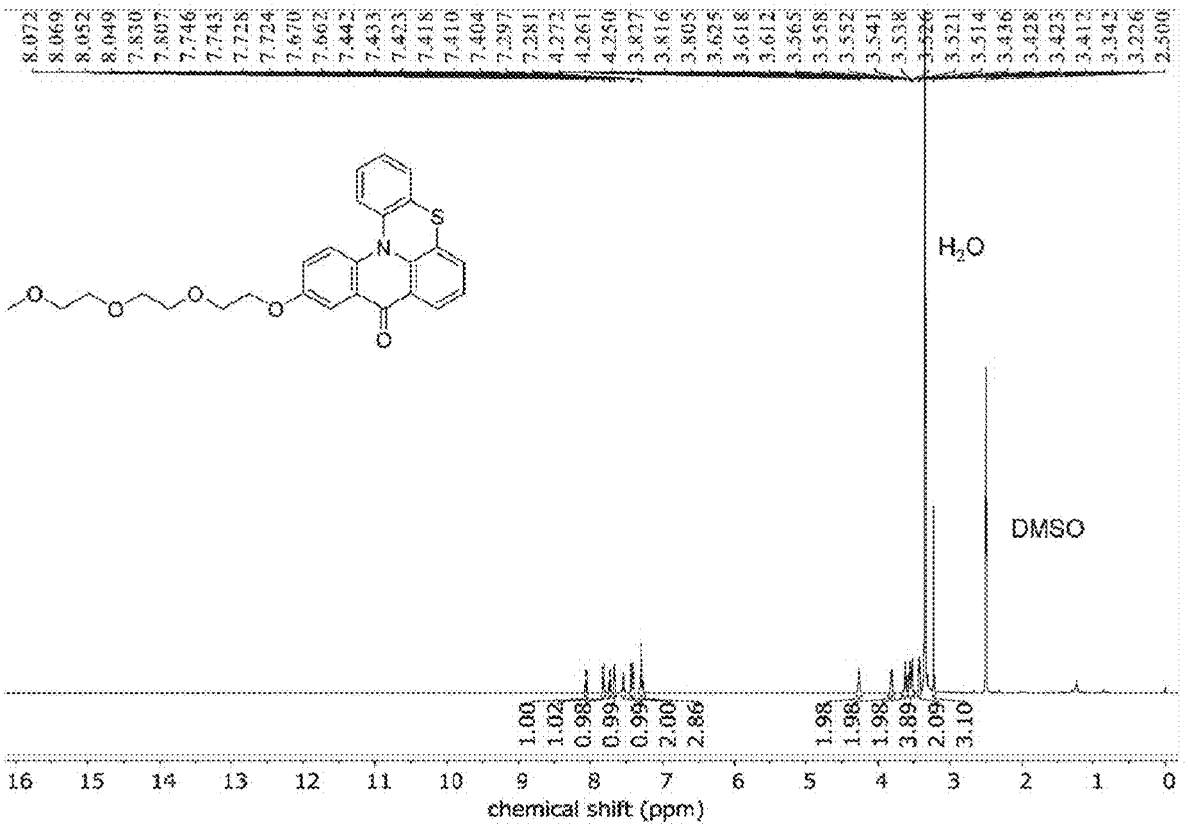
FIG. 4 is a nuclear magnetic resonance $^{1}H$ spectrum of QPT-TEG prepared in Embodiment 2.

NMR characterization of QPT-TEG obtained in Embodiment 4 is performed, and the results are shown in FIG. 4. In the NMR $^1H$ spectrum of QPT-TEG, $^1H$ NMR (400 MHz, DMSO-d6, ppm) δ=8.06 (dd, J=8.0, 1.4 Hz, 1H), 7.82 (d, J=9.2 Hz, 1H), 7.74 (dd, J=7.4, 1.4 Hz, 1H), 7.67 (d, J=3.0 Hz, 1H), 7.57-7.52 (m, 1H), 7.45-7.40 (m, 2H), 7.32-7.25 (m, 3H), 4.29-4.24 (m, 2H), 3.84-3.80 (m, 2H), 3.62 (dd, J=5.7, 3.1 Hz, 2H), 3.58-3.50 (m, 4H), 3.42 (dd, J=5.8, 3.7 Hz, 2H), 3.23 (s, 3H).

Figure 5:
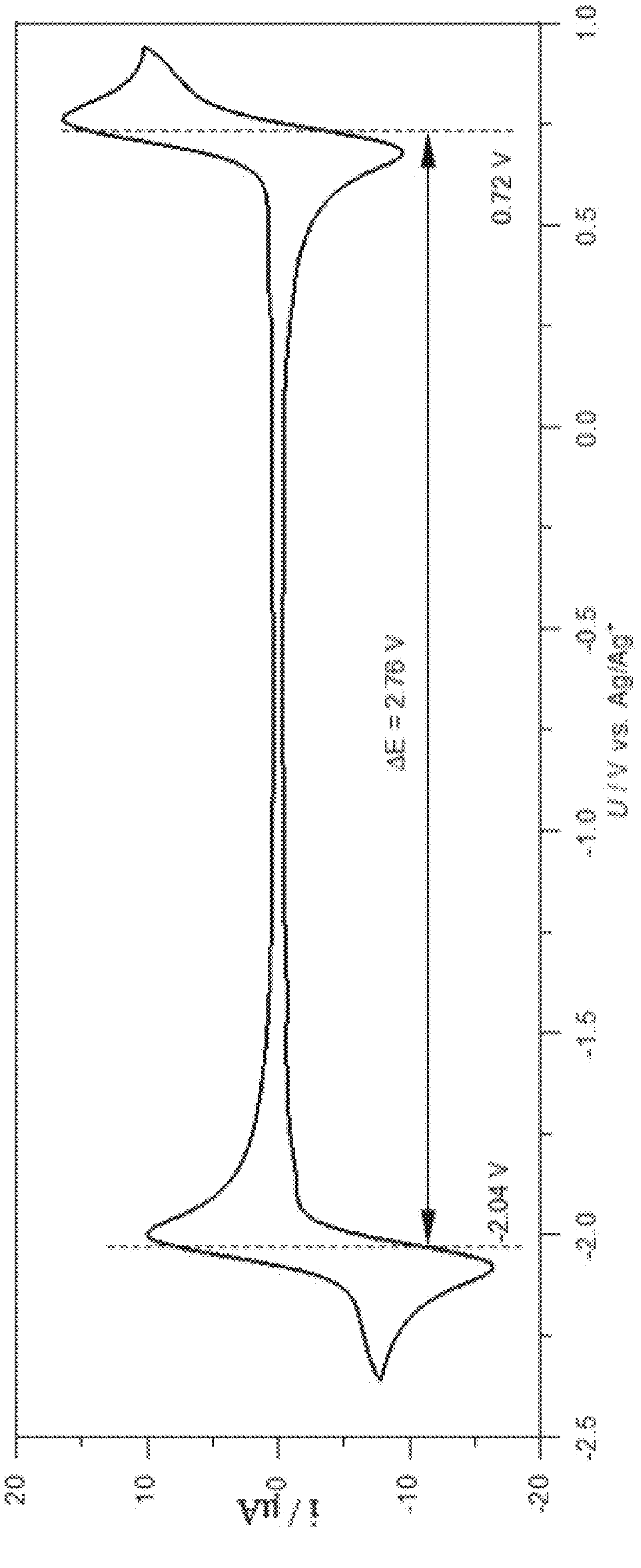
FIG. 5 is a cyclic voltammetric test curve of QPT-TEG prepared in Embodiment 2.

The redox kinetics of QPT-TEG obtained in Embodiment 4 is tested by cyclic voltammetry (CV). Tetrabutylammonium bis(trifluoromethylsulfonyl)imide (TBA-TF SI) is used as a supporting electrolyte and acetonitrile as a solvent. As shown in FIG. 5, the redox behavior of QPT-TEG is basically the same as that of QPT-OMe.

Test Example 3: Mixture of QPT-OMe and QPT-TEG

Figure 6:
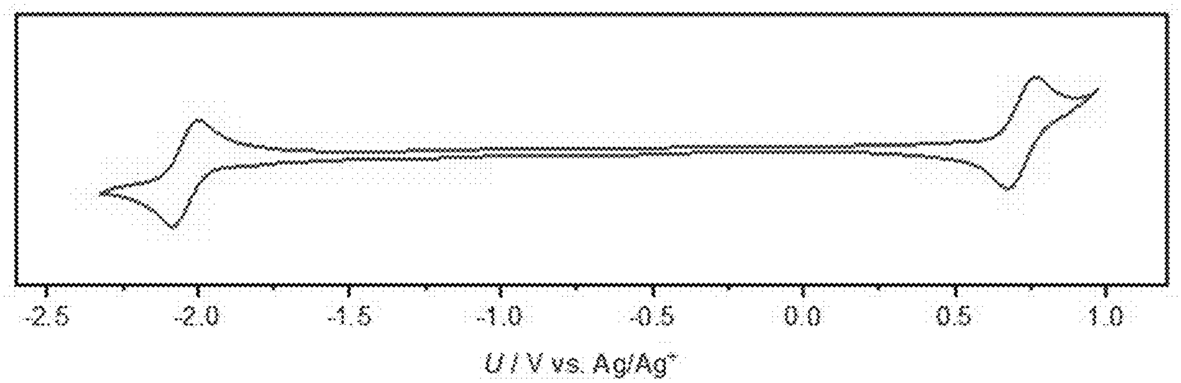
FIG. 6 is a cyclic voltammetric test curve of a mixture of QPT-OME and QPT-TEG.

QPT-OMe obtained in Embodiment 1 and QPT-TEG obtained in Embodiment 2 are mixed in a 1:1 molar ratio, and the mixture is subjected to electrochemical cyclic voltammetry tests, and the results are shown in FIG. 6, where the waveforms of the two materials completely overlap, indicating that functionalization using polar groups is an easy and effective way to increase the energy density without severely altering the redox of the QPT nuclei behavior and electronic configuration.

Application Example 1: QPT-OMe-Based Bipolar Static Flow Battery

The acetonitrile mixture of QPT-OMe and TBA-TFSI made in Embodiment 1 is used as cathode and anode electrolytes (where the concentrations of QPT-OMe and TBA-TFSI are 0.025 M and 0.5 M, respectively), and a porous membrane Daramic AA-800 is used as a membrane and graphite carbon felt is used as a collector to form a static flow battery.

Figure 7:
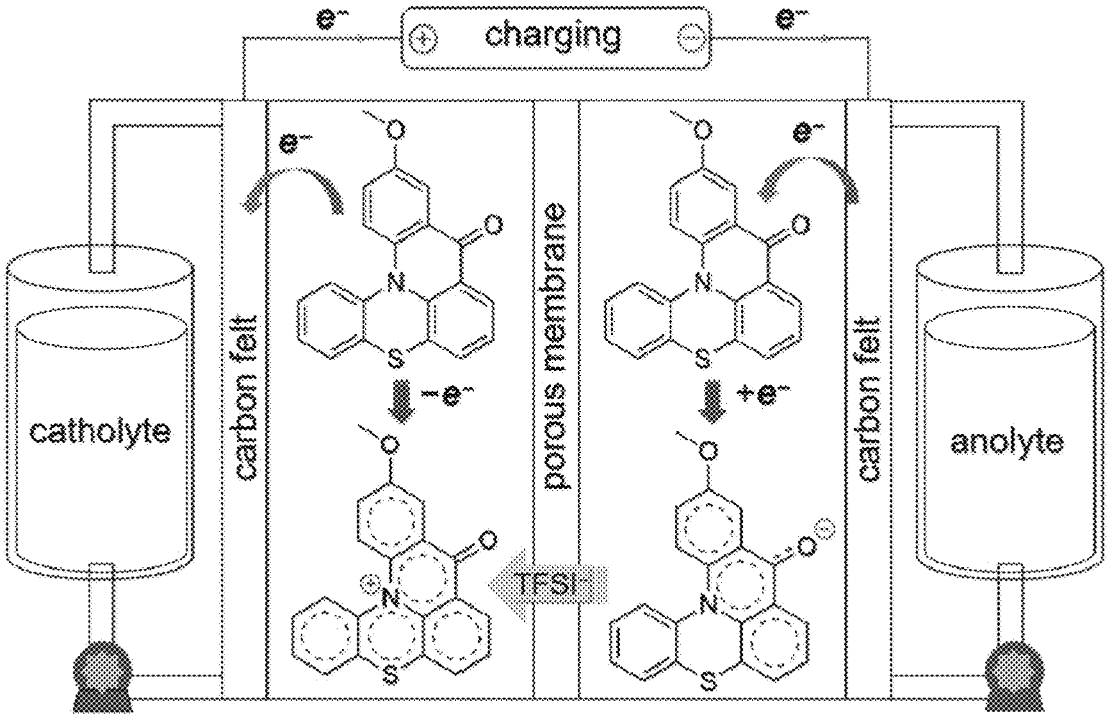
FIG. 7 is a schematic diagram of a battery structure and an electrochemical process during battery charging of an QPT-OMe-based bipolar flow battery.

FIG. 7 is a schematic diagram of a battery structure and an electrochemical process during battery charging of an QPT-OMe-based bipolar static flow battery.

0.1 mL of electrolyte is injected into both the cathode and anode reservoirs of the battery, and the charging and discharging cycles are tested with a charging current density of 5 mA $cm^{-1}$ and a discharging current density of 5 mA $cm^{-1}$. The test results are shown in FIGS. 8 to 10.

Figure 8:
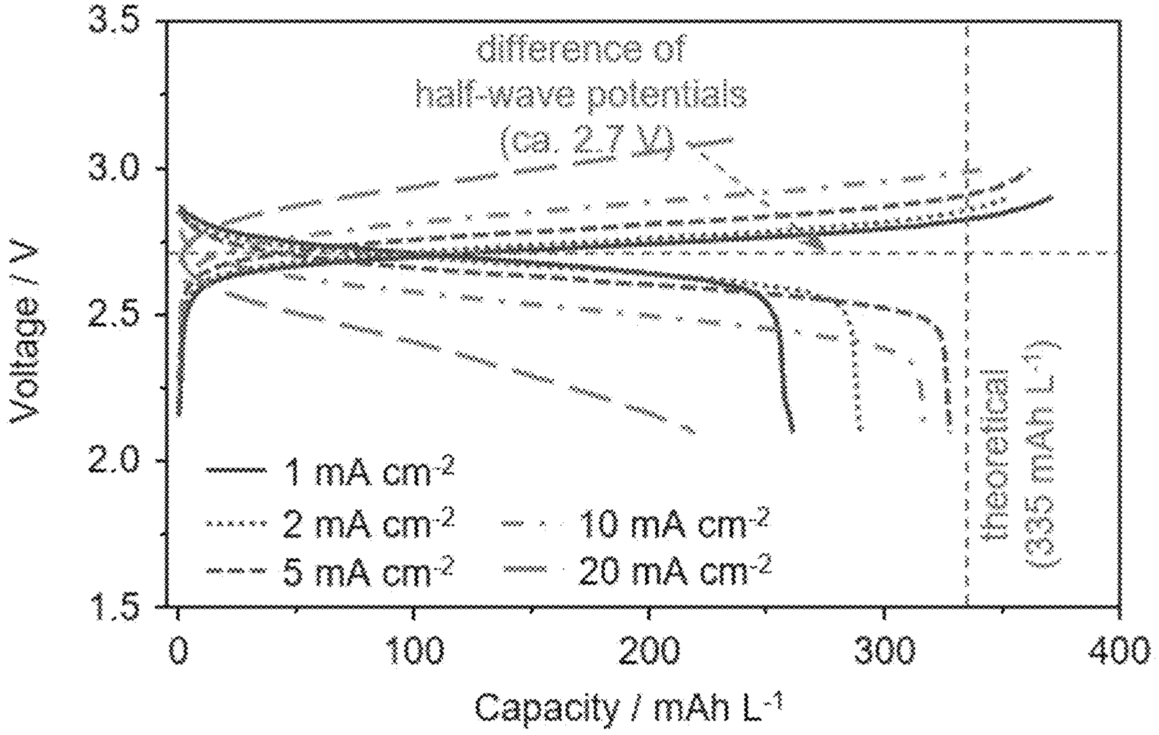
FIG. 8 shows representative charge and discharge curves of an QPT-OMe-based bipolar static flow battery at different current densities.

FIG. 8 shows representative charge and discharge curves of an QPT-OMe-based bipolar static flow battery at different current densities. A clear charging/discharging plateau is exhibited at all measured current densities. At low current densities (<5 mA $cm^{-1}$), the discharge voltage is 2.5 to 2.7 V, which is one of the highest values of discharge voltage available for RFBs. At high current densities of 20 mA $cm^{-2}$, the battery exhibits dense differential polarization due to limited mass transfer in the electrolyte and across the membrane. The utilization rates of QPT-OMe at current densities of 1, 2, 5, 10 and 20 mA $cm^{-2}$ are 77.6, 86.3, 94.3, 97.6 and 65.4%, respectively, with corresponding coulombic efficiencies (CE) of 70.0, 82.1, 90.6, 92.9 and 92.8%, respectively. At a current density of 20 mA $cm^{-2}$, the utilization rate decreases, which may be due to the increase in mass transfer limitation and voltage hysteresis, but the CE still increases due to the shortened charge/discharge time.

Figure 9:
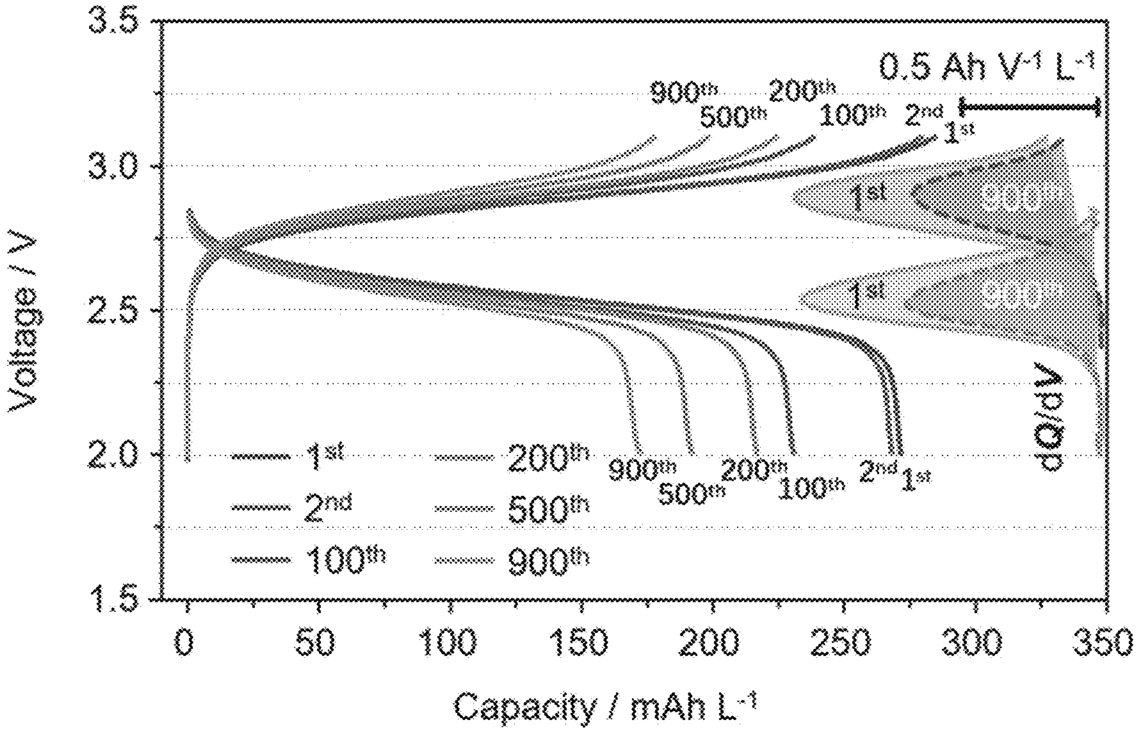
FIG. 9 shows selected charge and discharge curves during a long cycle for an QPT-OMe-based bipolar static flow battery.

FIG. 9 shows selected charge and discharge curves during a long cycle for an QPT-OMe-based bipolar static flow battery. The voltage plateau remains almost constant over 900 cycles, which is further demonstrated by the differential capacity analysis shown in the inset on the right side of FIG. 9, where the potential ranges as well as the peak positions for the charging (2.7 to 3.1 V) and discharging (2.4 to 2.7 V) processes do not change over long periods of time.

Figure 10:
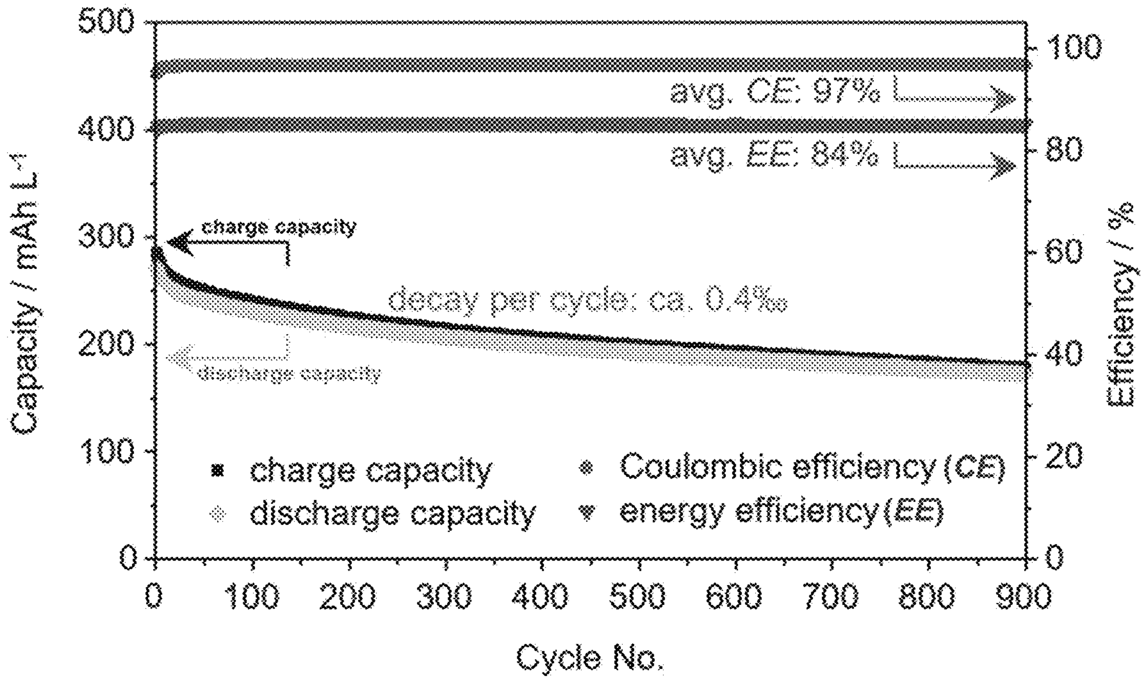
FIG. 10 shows corresponding capacity retention, coulombic efficiency, and energy efficiency for an QPT-OMe-based bipolar static flow battery.

FIG. 10 shows corresponding capacity retention, coulombic efficiency, and energy efficiency for an QPT-OMe-based bipolar static flow battery. After 900 cycles, the capacity retention of the battery is about 63.5%, the decay rate is about 0.4%0 per cycle, and the coulombic efficiency and energy efficiency reach about 97% and 84%, respectively. The presented performance is superior to most non-aqueous phase flow batteries that use BRM or asymmetric organic molecules as active materials.

A polarity reversal test is performed by filling 0.1 mL of electrolyte into both the cathode and anode reservoirs of the battery with a charging current density of 5 mA $cm^{-1}$ and a discharging current density of 5 mA $cm^{-1}$. The polarity of the battery is reversed every 50 cycles, and the current is reversed 4 times before 300 cycles. The test results are shown in FIGS. 11 to 13.

Figure 11:
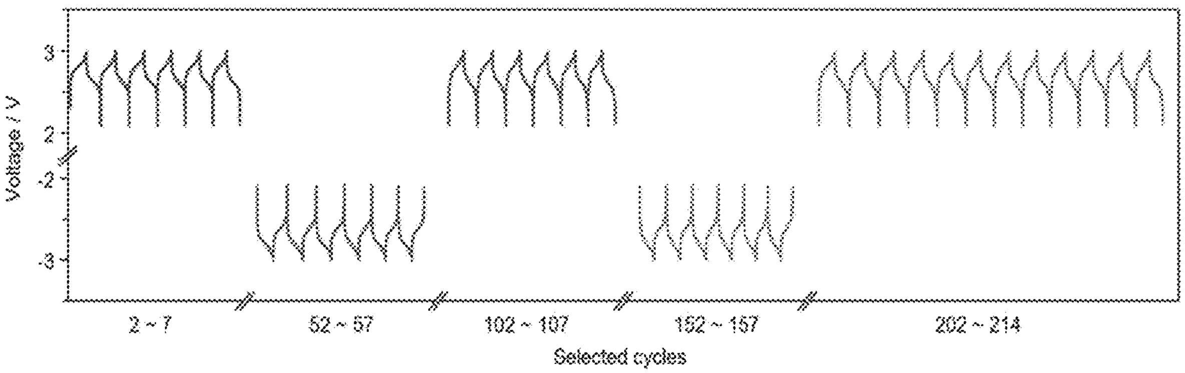
FIG. 11 shows representative constant current charge/discharge curves for an QPT-OMe in a bipolar static flow battery in a polarity reversal test.

FIG. 11 shows representative constant current charge/discharge curves for an QPT-OMe in a bipolar static flow battery in a polarity reversal test.

Figure 12:
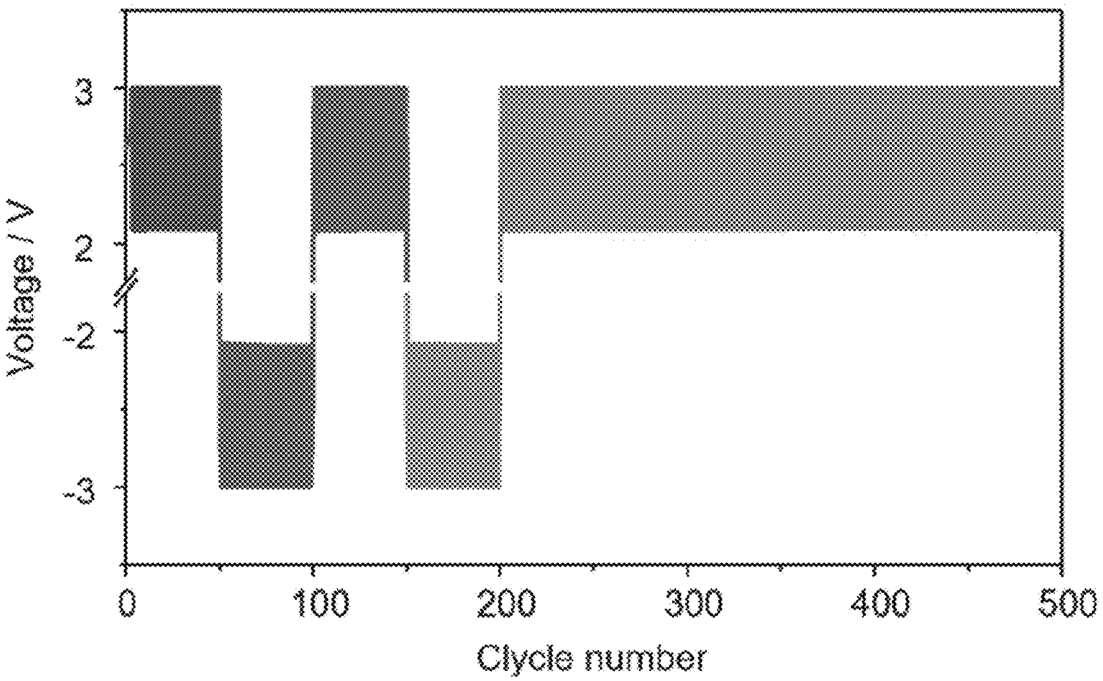
FIG. 12 shows long cycle battery charge/discharge curves of an QPT-OMe in a bipolar static flow battery in a polarity reversal test.

FIG. 12 shows long cycle battery charge/discharge curves of an QPT-OMe in a bipolar static flow battery in a polarity reversal test.

Figure 13:
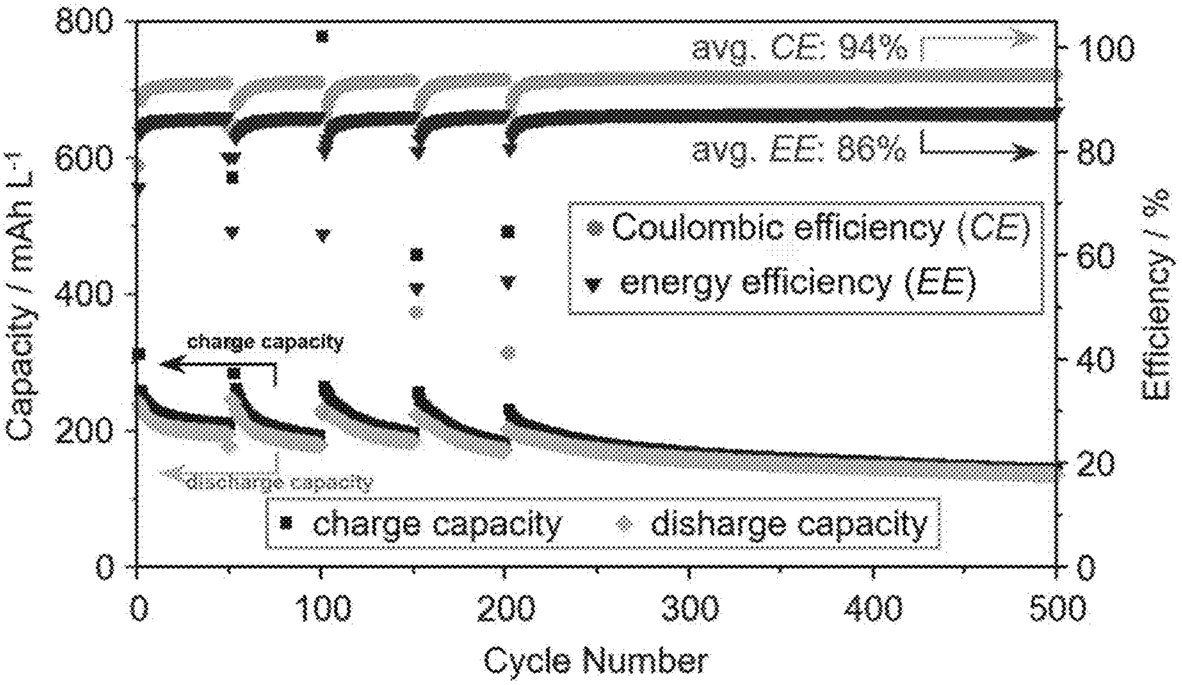
FIG. 13 shows corresponding charge/discharge capacity, coulombic efficiency, and energy efficiency of an QPT-OMe in a bipolar static flow battery in a polarity reversal test.

FIG. 13 shows corresponding charge/discharge capacity, coulombic efficiency, and energy efficiency of an QPT-OMe in a bipolar static flow battery in a polarity reversal test.

The charge/discharge curves (FIGS. 11 and 12) exhibit a high degree of symmetry throughout the cycle and no deviation is observed between two consecutive charge or discharge cycles. 56% capacity retention is achieved, and the coulombic efficiency and energy efficiency are maintained at approximately 94% and 86%, respectively, after 500 cycles (FIG. 13).

Application Example 2: QPT-OMe-Based Bipolar Dynamic Flow Battery

The acetonitrile mixture of QPT-OMe and TBA-TFSI made in Embodiment 1 is used as cathode and anode electrolytes (where the concentrations of QPT-OMe and TBA-TFSI are 0.025 M and 0.5 M, respectively), and a porous membrane Daramic AA-800 is used as a membrane and graphite carbon is used as a collector to form a dynamic flow battery.

3 mL of electrolyte is injected into both the cathode and anode reservoirs of the battery, and a circulation pump is started to make the electrolyte flow from the reservoir through a circulation pipe to the cathode and anode of the battery, and the charging and discharging cycles are tested with a charging current density of 10 mA $cm^{-1}$ and a discharging current density of 10 mA $cm^{-1}$. The test results are shown in FIGS. 14 to 15.

Figure 14:
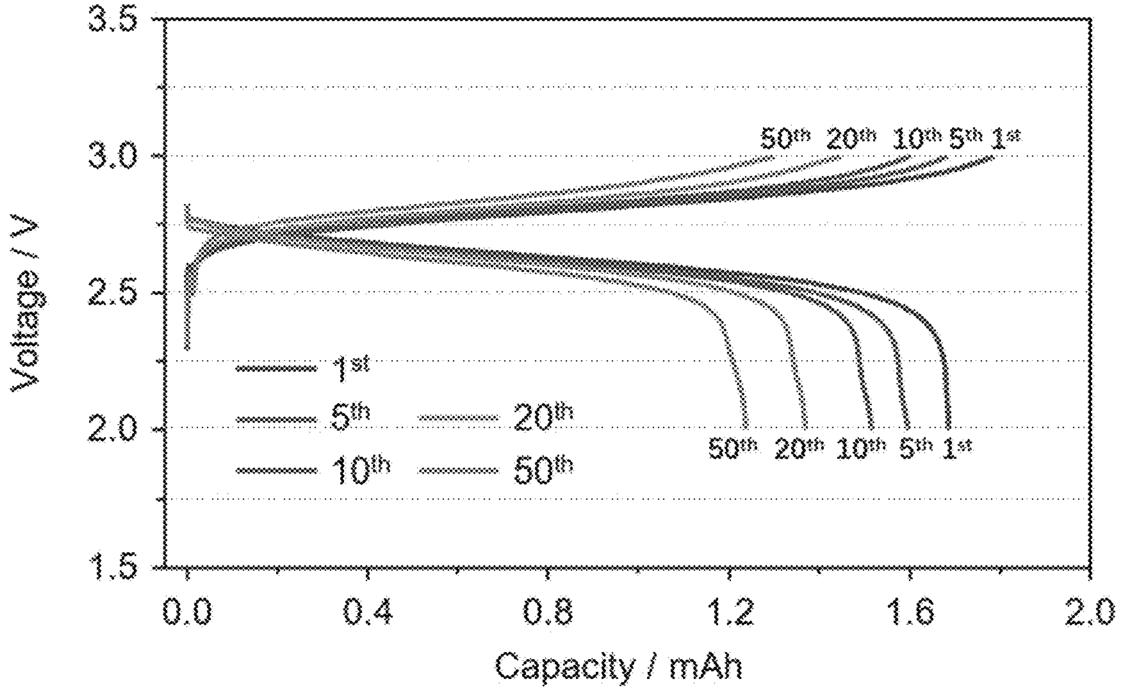
FIG. 14 shows selected charge/discharge curves during a long cycle for an QPT-OMe-based bipolar dynamic flow battery.

FIG. 14 shows selected charge/discharge curves during a long cycle for an QPT-OMe-based bipolar dynamic flow battery. The voltage plateau remains almost constant over 50 cycles. The charge/discharge curves are the same as FIG. 9, with a first utilization rate of 83.5%.

Figure 15:
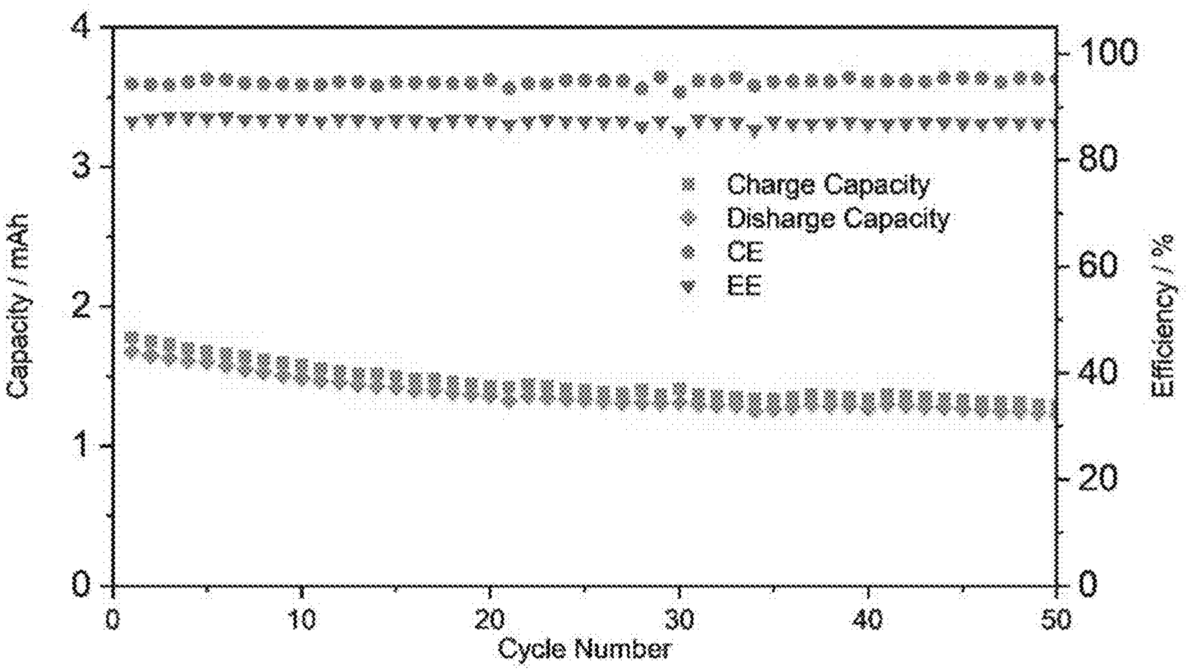
FIG. 15 shows capacity retention, coulombic efficiency, and energy efficiency of an QPT-OMe-based bipolar dynamic flow battery.

FIG. 15 shows capacity retention, coulombic efficiency, and energy efficiency of an QPT-OMe-based bipolar dynamic flow battery. The capacity retention of the battery is about 73.8%, and the coulombic efficiency and energy efficiency are maintained at 95% and 87%, respectively, after 50 charge and discharge cycles.

Application Example 3: QPT-TEG-Based Bipolar Static Flow Battery

An acetonitrile mixture of QPT-TEG and TBA-TFSI made in Embodiment 4 is used as cathode and anode electrolytes (where the concentrations of QPT-TEG and TBA-TFSI are 0.5 M and 0.5 M, respectively), and a porous membrane Daramic AA-800 is used as a membrane and graphite carbon is used as a collector to form a static flow battery.

0.1 mL of electrolyte is injected into both the cathode and anode reservoirs of the battery, and the charge and discharge cycles are tested with a charge current density of 5 mA $cm^{-1}$ and a discharge current density of 5 mA $cm^{-1}$. The test results are shown in FIGS. 16 to 17.

Figure 16:
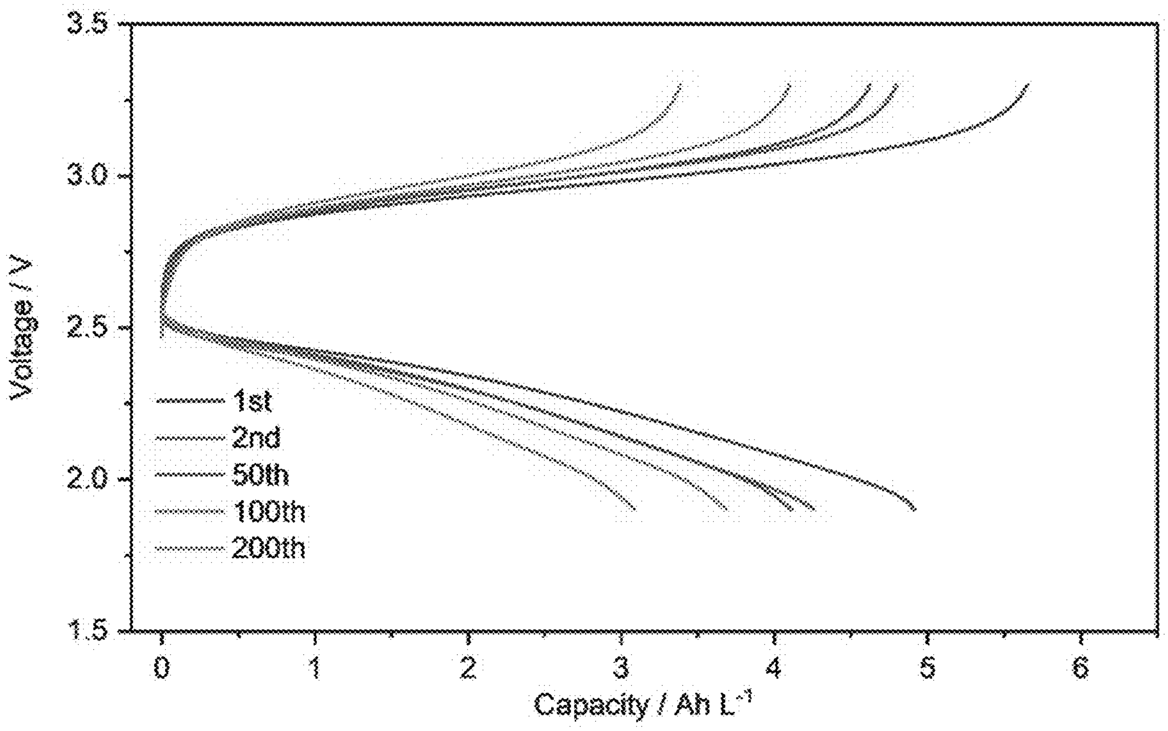
FIG. 16 shows selected charge/discharge curves during a long cycle for an QPT-TEG based bipolar static flow battery.

FIG. 16 shows selected charge/discharge curves during a long cycle for an QPT-TEG based bipolar static flow battery. The voltage plateau is maintained at about 2.3 V during discharge.

Figure 17:
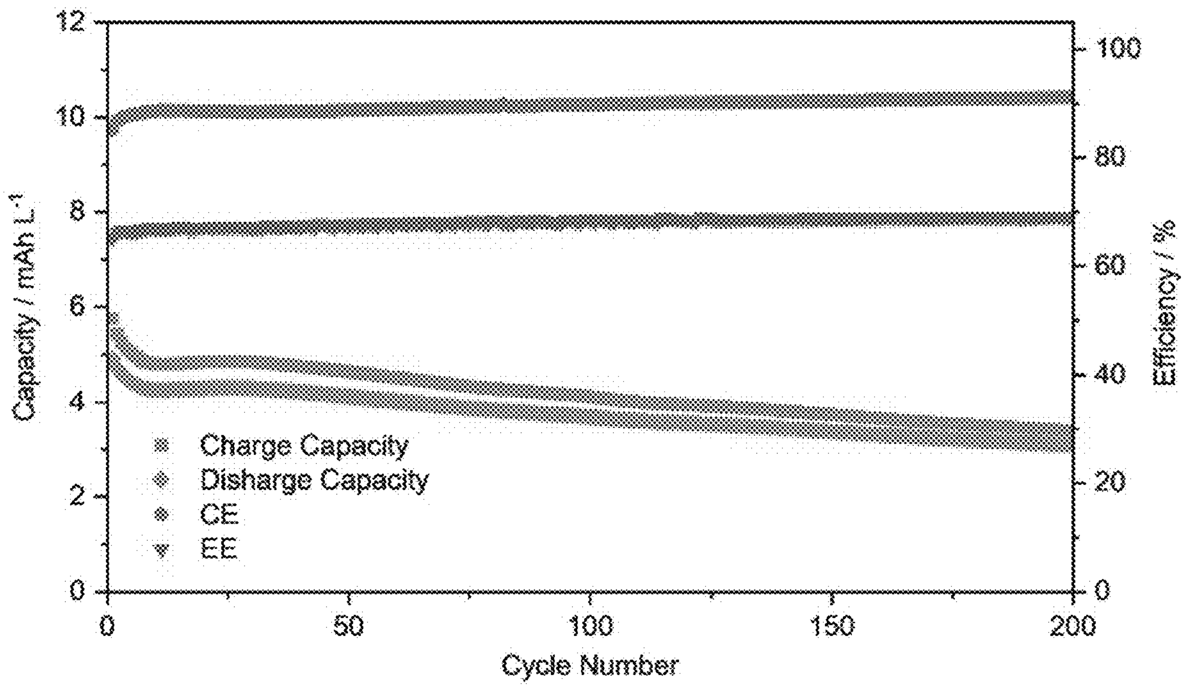
FIG. 17 shows capacity retention, coulombic efficiency, and energy efficiency of an QPT-TEG-based bipolar static flow battery.

FIG. 17 shows capacity retention, coulombic efficiency, and energy efficiency of an QPT-TEG-based bipolar static flow battery. The utilization of active substance in the first cycle is 74.6%, and the discharge capacity remained 63% after 200 cycles. Compared with low concentration batteries, both the active substance utilization and capacity retention decreases, which is common in RFBs using high concentration electrolytes.

The raw materials and equipment used in the present disclosure, if not otherwise specified, are commonly used in the field; the methods used in the present disclosure, if not otherwise specified, are conventional methods in the field.

The above mentioned is only prefer embodiments of the present disclosure, not any limitation of the present disclosure, and any simple modification, change and equivalent transformation of the above embodiment according to the technical substance of the present disclosure are still within the scope of the technical solution of the present disclosure.

What is claimed is:

1. A conjugation-fused bipolar redox-active molecule having a structural formula of

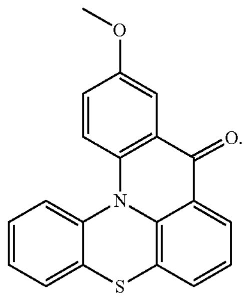 [SMILES: COc1ccc2c(c1)c(=O)c1cccc3c1n2-c1ccccc1S3]

2. A conjugation-fused bipolar redox-active molecule having a structural formula of

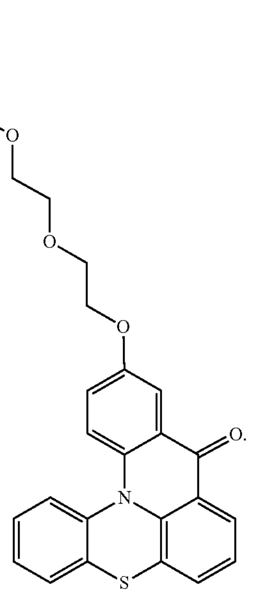

* * * * *